(12) United States Patent
James et al.

(10) Patent No.: US 10,786,467 B1
(45) Date of Patent: Sep. 29, 2020

(54) SHELF STABLE DOSAGE OF DESSICATED SUGAR MATRIX INFUSED WITH GINGEROL AND SHOGAOL

(71) Applicant: Enteral Health and Nutrition LLC, Chesterfield, MO (US)

(72) Inventors: Dustin Garth James, Fairview, TX (US); Helen Kim-James, Fairview, TX (US)

(73) Assignee: Enteral Health and Nutrition, LLC, Ellisville, MO (US)

( * ) Notice: Subject to any disclaimer, the term of this patent is extended or adjusted under 35 U.S.C. 154(b) by 710 days.

(21) Appl. No.: 15/370,246

(22) Filed: Dec. 6, 2016

Related U.S. Application Data

(63) Continuation-in-part of application No. 14/091,877, filed on Nov. 27, 2013, now abandoned, which is a continuation-in-part of application No. 13/328,114, filed on Dec. 16, 2011, now abandoned.

(60) Provisional application No. 61/490,203, filed on May 26, 2011.

(51) Int. Cl.
*A61K 31/12* (2006.01)
*A61K 9/00* (2006.01)
*A61K 47/26* (2006.01)
*A61K 36/9068* (2006.01)

(52) U.S. Cl.
CPC .............. *A61K 31/12* (2013.01); *A61K 9/006* (2013.01); *A61K 36/9068* (2013.01); *A61K 47/26* (2013.01)

(58) Field of Classification Search
CPC .............................. A61K 36/906; A61K 47/26
See application file for complete search history.

(56) References Cited

U.S. PATENT DOCUMENTS

| | | | |
|---|---|---|---|
| 6,306,429 | B1 | 10/2001 | Bealin-Kelly |
| 6,673,380 | B2 | 1/2004 | Yang et al. |
| 7,214,396 | B2 | 5/2007 | Rivier |
| 7,531,192 | B2 | 5/2009 | Farber et al. |
| 2003/0077362 | A1 | 4/2003 | Panhorst |
| 2006/0222722 | A1 | 10/2006 | Roberts |
| 2012/0258058 | A1 | 10/2012 | Herrmann |
| 2013/0251805 | A1 | 9/2013 | Tuula |

OTHER PUBLICATIONS

"Passover ginger candy". Internet date: 2008. [Retrieved from the internet on: Aug. 5, 2019]. Retrieved from: <URL:http://jedzenie.dookolaswiata.eu/przepisyp.php?s=30&np=12&id=3407>. (Year: 2008).*

"The cold water candy test". Archive date: Dec. 17, 2002. [Retrieved from the internet on: Aug. 5, 2019]. Retrieved from: <URL: http://web.archive.Org/web/20021217015432/http://www.exploratorium.edu/cooking/candy/sugar-stages.html>. (Year: 2002).*

Peter G Welling, Influence of Food and Diet on Gastrointestinal Drug Absorption, a Review, J. of Pharmacokinetics and Biopharmaceutics, vol. 5, No. 4, 1977.

James C McElnay, Drug Delivery Buccal Route, Encyclopedia of Pharmaceutical Technology, Chapter 27, 2007.

Suzanna M Zick, Pharmacokinetics of 6-Gingerol, 8-Gingerol, 10-Gingerol, and 6-Shogaol and Conjugate Metabolites in Healthy Human Subjects, Cancer Epidemiol Biomarkers Prev 2008;17:1930-1936.

Jeong Kim, [6]-Gingerol Induces Apoptosis in Oral Cavity Cancer Cells, Otolaryngology—Head and Neck Surgery 2010 143: P155 DOI: 10.1016/j.otohns.2010.06.254.

Suzanna M Zick, Pharmacokinetics of 6-Gingerol, 8-Gingerol, 10-Gingerol, and 6-Shogaol and Conjugate Metabolites in HealthyHuman Subjects, Cancer Epidemiol Biomarkers Prev 2008;17(8). Aug. 2008.

V. Baskar, Study on Improving Bioavailability Ratio of Anti-Inflammatory Compound From Ginger Through Nano Transdermal Delivery, Asian Journal of Pharmaceutical and Clinical Research vol. 5, Issue 3, 2012 ISSN-0974-2441.

S.V. Nampoothiri, Comparison of Essential Oil Composition of Three Ginger Cultivars from Sub Himalayan Region, Asian Pacific Journal of Tropical Biomedicine, (2012)S1347-S1350.

Assessment report on Zingiber officinale Roscoe, rhizoma, Mar. 27, 2012 EMA/HMPC/577856/2010 Committee on Herbal Medicinal Products (HMPC).

* cited by examiner

*Primary Examiner* — Amy L Clark
(74) *Attorney, Agent, or Firm* — Linda L. Lewis

(57) ABSTRACT

The present invention is a method of preparing a buccal delivery system for treating digestive distress comprising heating a sugar base to lower the water content to about less than or equal to 5 wt. %, removing the sugar base from the heat source, adding the non-volatile ginger extract having at least 10% gingerol by weight, adding the gingerol active to the hot sugar matrix and converting it into a ratio of gingerol and shogaol, ambient cooling the base to a malleable form in which individual dosages are shaped, wherein the gingerol and shogoals are present in an amount and ratio of from 2:1 to 10:1 gingerol to shogoals; where the gingerol and newly formed shogaols are immediately released; and where the typical dosage of the combination is in the range of about 1.0 to 5.4 g.

5 Claims, 1 Drawing Sheet

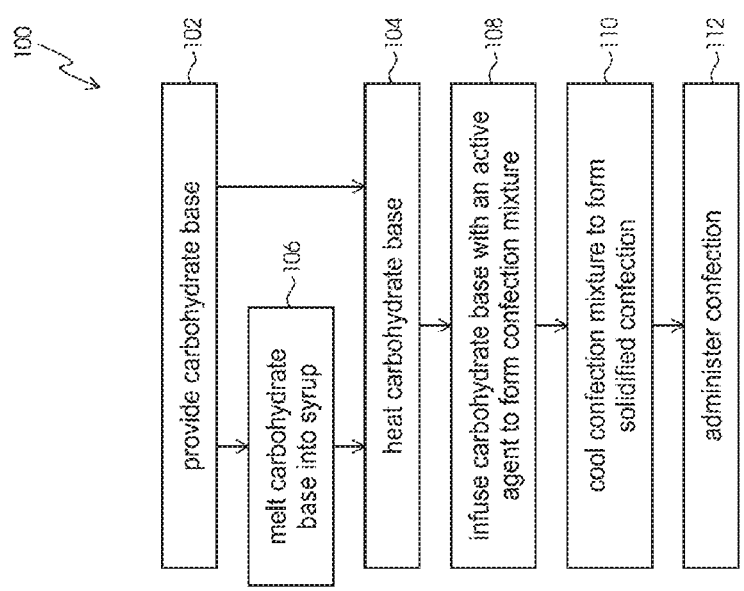

SHELF STABLE DOSAGE OF DESSICATED SUGAR MATRIX INFUSED WITH GINGEROL AND SHOGAOL

CROSS-REFERENCE TO RELATED APPLICATIONS

The present application claims priority to U.S. Utility application Ser. No. 14/091,877 filed Nov. 27, 2013, which is hereby incorporated by reference, which claims priority to U.S. Utility application Ser. No. 13/328,114 filed Dec. 16, 2011, which is hereby incorporated by reference, which claims priority to U.S. Provisional Application Ser. No. 61/490,203 filed May 26, 2011 and having the title "METHOD OF ASSISTING WITH DIGESTIVE UPSETS USING A CONFECTION-BASED DELIVERY OF PEPPERMINT OIL AND GINGER", which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to the treatment of digestive upsets by the buccal administration of a shelf-stable combination of specific non-volatile derivatives of *Zingiber officinale*, also known as ginger root, in a desiccated sugar matrix.

Related Art

Botanicals are often consumed with the intention of improving an aspect of human health. As fresh botanicals have large variations in availability and quality, issues with spoilage, and very low concentrations of desirable bioactive chemicals, botanical derivatives are often consumed instead. Botanical derivatives, including teas, powders, extracts and essential oils have been used for treating digestive upsets. The challenge in using the botanical derivatives is consuming enough of the active ingredient to provide the desired digestive relief. In addition, most botanicals contain numerous active compounds that users cannot easily manipulate for a desired health effect. Many botanical derivatives which have concentrated active compounds, such as essential oils and extracts, are harsh and irritating to the mucosa of the gastrointestinal tract. When doses are sufficiently large to be effective, the organoleptic properties are too unpleasant and/or irritating. In addition, many botanicals, including ginger, degrade with time and exposure to moisture, which leads to a diminished clinical effect. As a result, many have a limited shelf life. The present invention overcomes all of these shortcomings.

There has been an approach of taste-masking the botanical derivatives to deliver them in sufficient quantity to be effective. One such approach is to encapsulate the active. However, when a capsule is used, the delivery of the active is not immediate, as the capsule needs to be ingested and then released into the stomach and small intestine for absorption. Others include application of coatings aimed at diminishing the negative organoleptic characteristics such as bitterness, astringency, and pungency. This methods fails to mask the undesirable organoleptic properties after the coating has been consumed, and also increase the complexity and time utilized in such formation. It is desirable to have an immediate release dosage, as many digestive complaints present suddenly. Additionally, it is desirable to have the botanical active absorbed before reaching the stomach and small intestine so that the digestive system does not break down the active. In addition, the rapid absorption of the botanical active from the buccal route is desirable in that it bypasses first-pass hepatic metabolism. Active botanicals absorbed from the stomach and small intestine are subject to degradation by the liver before they enter the systemic circulation. In the buccal route, the rich vascular supply of the buccal mucosa and salivary glands directly feeds into the jugular venous system which directly drains into the heart for systemic circulation.

In addition, botanicals often contain both a volatile component, commonly referred to as essential oils, and a non-volatile component. Each may have a biologic effect that is distinct from the other. For instance, in *Zingiber officinale*, the compounds shown to be effective in reducing digestive complaints such as nausea are found in the non-volatile extract and belong predominantly to the gingerol family of compounds. The volatile compounds found in ginger essential oil are essentially devoid of gingerol. Each component has distinct physical properties that must be taken into account when incorporating into a product intended for biologic use. For instance, a compound utilizing *Zingiber officinale* essential oil will have the characteristic taste of ginger secondary to the volatile nature of this extract, but be devoid of the desired biologic activity to reduce digestive complaints. A compound utilizing the non-volatile gingerol rich extract will have the potential to have biological activity to assist with digestive complaints, but will also have an intense pungency inherent to these compounds, which makes is undesirable for ingestion.

Moreover, some botanicals contain active compounds that may degrade or convert to other biologically active compounds. Each of these new compounds may themselves exhibit biologic activity. In addition, specific ratios of these compounds, both parent and child, can have distinct effects on biologic processes and complaints. In particular, the main non-volatile biologically active compounds of *Zingiber officinale*, gingerols, can undergo transformation into shogaols, which have distinct desired biologic activity, as well as zingerone, which does not carry the same desired biologic activities. In addition, specific manipulation of water content and temperature can be utilized to produce specific ratios of compounds that have a desired effect.

Finally, an additional shortcoming of traditional methods of delivery of botanical extracts with specific biologic activity is limited shelf-life stability. Most botanicals will degrade into biologically inactive substances with time, and through temperature and humidity dependent processes. This is true for *Zingiber officinale*, in which gingerols spontaneously degrade into undesirable compounds under ambient conditions. It is desirable to incorporate the *Zingiber officinale* extract into a stable matrix with minimal water content and minimal ambient air exposure in order to extend shelf life. Common forms of dietary supplements, including encapsulation in pill form and teas/tisanes, do not avoid these deteriorating conditions. An ideal delivery matrix would be almost devoid of moisture, limit air exposure, and be resistant to spoilage by microorganisms.

For the present invention, we present a method to transform a non-volatile gingerol rich extract from *Zingiber officinale* into a specific ratio of gingerols to shogaols in a shelf-stable form that can be taken through buccal and oral administration to assist with digestive complaints. Analysis at 33 month post production of the invention revealed a stable dosage without evidence of spoilage.

The present buccal delivery system provides the required dose of the gingerol:shogaol ratio in an organoleptically pleasing form that is immediately released and exhibits extended shelf-life stability. While some of the derivative may be swallowed as it dissolves in the mouth, there is absorption through the membranes of the mouth, throat, and salivary glands, thereby by-passing the degradation and latency of the luminal digestive system.

The present buccal delivery system provides unencapsulated biologically active *Zingiber officinale* derivatives of gingerol and shogaol in specific ratio in an immediate release form that are in a sufficiently high dosage to be effective in relieving digestive distress. The dosage form is a desiccated simple sugar combination delivery system, and the *Zingiber officinale* extract is added immediately after the process of heating the sugar base to remove the moisture. The temperatures range from about 270° F. to about 310° F., preferably in the 300° F. to 310° F. range. A specific non-volatile extract of *Zingiber officinale* normalized to at least 10% gingerol is added once about 95-99.5 wt. % water has been driven out, as indicated by the temperature of the sugar base, and the sugar has been removed from the heat source. This gingerol enriched extract melts and incorporates in a uniform manner in the sugar matrix through the act of stirring. The gingerol then converts in these conditions of heat and desiccation into a combination of gingerol and shogaol.

Adequate amounts of the gingerol enriched extract are added to the desiccated sugar matrix base such that the amount and ratio of these compounds has the desired biologic activity and remains palatable. The typical range is from 0.25% to 0.50% by weight of 10% gingerol extract added to the heated and desiccated sugar matrix. The amount of gingerol active added is from about 0.025 wt. % to 0.050 wt. %. Optionally, natural flavorings are added during the process to make the dose palatable. The range of flavorings added is from about 0.002% to 1.0% by weight.

The present invention is a solid buccal delivery system for treating digestive distress comprising a desiccated sugar matrix infused with a nonvolatile extract from *Zingiber officinale*, wherein the extract has a concentrated gingerol component normalized to at least 10%; wherein the gingerol undergoes transformation into a specific ratio of gingerol and shogaols through heating in a desiccated environment, and wherein the gingerol and shogaols are present in the sugar base in the range of from about 0.025 to about 0.050 wt. %; and a dosage size of from about 1.0 to 5.4 grams to deliver from about 0.25 mg to 2.7 mg of gingerol and shogaols per dosage to provide relief of the digestive distress. The *Zingiber officinale* derivatives are not encapsulated, and the active compounds, including gingerol and shogaol, are immediately released in the oral cavity. Immediate release is understood in the art to be at least partially released in about 15 minutes or less.

SUMMARY OF THE INVENTION

The present invention further comprises a method of preparing a buccal delivery system for treating digestive distress comprising heating a sugar base to lower the water content to about less than or equal to 5 wt. %, removing the sugar base from the heat source, adding the non-volatile extract from *Zingiber officinale* normalized to at least 10% gingerol by weight, transforming the gingerol component into a ratio of gingerol and shogaol by adding the gingerol active to the hot sugar matrix, shaping the resulting combination into desired forms, and ambient cooling the base to a malleable form in which individual dosages are shaped, further ambient cooling to form a solid dosage, wherein the gingerol and shogoals are present in an amount and ratio of from 2:1 to 10:1 gingerol to shogoals, which is sufficient to provide relief of the digestive distress, where the gingerol enriched *Zingiber officinale* extract is not encapsulated, and where the *Zingiber officinale* extract derivatives, including gingerol and newly formed shogaols are immediately released. The typical dosage of the combination of desiccated sugar base and gingerol shogaol combination is in the range of about 1.0 to 5.4 g.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawing. The drawing constitutes a part of this specification and includes exemplary embodiments of the invention, which may be embodied in various forms. In addition, in the embodiments depicted herein, like reference numerals in the various drawings refer to identical or near identical structural elements.

FIG. 1 is a flowchart of a method for forming the desiccated sugar base dosage for digestive disorders.

DETAILED DESCRIPTION OF THE PREFERRED EMBODIMENTS

The following description of the preferred embodiment(s) is merely exemplary in nature and is in no way intended to limit the invention, its application, or uses.

On average, fresh botanicals contain about 95% water by weight. Of the remaining mass, biologically active compounds only represent a small percentage, typically less than 0.15% range by weight Fresh *Zingiber officinale* contains an average of 94% water by weight and 0.021% gingerol by weight It is impractical to consume fresh ginger in a clinically meaningful amount, as the quantities are much larger than encountered in normal circumstances. For instance, in order to obtain 10 mg of gingerol, one must consume 7,940 mg of fresh ginger. Moreover, the vast majority of biologically active non-volatiles compounds in *Zingiber officinale* are in the form of gingerols, and not shogaols, which have distinct and desirable biologic effects.

These same shortcomings are inherent to using dried botanicals as well. Dried botanicals, often referred to as culinary spices, contain from 0.16 wt. % to 7 wt. % by weight active beneficial compounds, with a typical range from 0.5% to 2.5% by weight. In *Zingiber officinale*, gingerol is present at 1.68% by weight. Although this form improves upon the shortcomings of using fresh ginger, it remains impractical. Specifically for *Zingiber officinale*, the chemical composition of desirable non-volatile compounds in the invention, namely gingerol and shogaol, is distinct and not equivalent to that found in the dried form.

Botanical extracts can be in the form of essential oil, powder, or a liquid are processed in some way to enrich the active compounds. These processes include steam distillation, supercritical $CO_2$ extraction, solvent extraction, or other methods. The active compounds are present in these extracts from about 10 wt. % to 100 wt. %. Since the active compounds are concentrated, small quantities ingested to consume the desired amount of active. However, prior art dosages have encapsulated these concentrates, because of the strong taste and irritating character. Encapsulation does not provide for rapid release of the active compounds into the body. In addition, for Zingiber officinale, the desirable non-volatile extracts are predominantly in the form of gingerol. The current invention provides for a method of covering a portion of this gingerol into shogaol, such that the resulting combination of gingerol and shogaol in the dosage is unique. This novel amount and ratio provides a unique method of assisting with digestive upsets. Indeed, it is important to note that the extraction and methods of processing of Zingiber officinale influences the chemical composition of the non-volatile compounds of the botanical. For example, fresh ginger is nearly devoid of shogaol, while ginger processed at prolonged high temperatures has significant amounts of shogaol. The differing ratios of gingerol to shogaol influence biology in distinct ways. For the purposes of assisting with digestive upsets, specific ratios of gingerol and shogaol are desirable.

In addition, botanicals are derived from plants which are subject to seasonal, variety, and cultivar specific factors. Essential oil composition of two unique ginger (Zingiber officinale Roscoe) cultivars from Sikkim and Aggarwal. The result is a large variance in the active compounds in the botanicals. The current invention has the benefit of controlling between varying concentrations of gingerol present in different varieties, cultivars and seasonal crops of Zingiber officinale. The extraction method normalizes the extracts to a specific percentage by weight of gingerol. In the current invention, the gingerol concentration is at least 10% by weight in the non-volatile extract, with a typical value of 10%.

The amount of active compounds present in one dose of the desiccated and infused sugar base can vary from about 0.5 mg to 10.0 mg. The amount of active compound added to the desiccated sugar base ranges from 0.01 to about 0.050 wt. %. Preferably, the amount of active compound present in the dosage is in the range from about 1.0 mg to 5.4 mg. The dosage weighs from about 1.0 to 5.4 g total, and preferably, from about 3.0 to 5.0 g, and most preferably 3.5 g. Lower dosages fail to provide soothing properties for stomach upset, and higher dosages are often too irritating. The addition of flavorings provides improved palatability of the invention such that clinically meaningful doses of active compounds could be more easily achieved. Specifically, for Zingiber officinale, the ideal embodiment involves adding the 10 wt. % gingerol non-volatile extract of Zingiber officinale to the desiccated sugar mixture in a range of 0.25% to 0.50% by weight. Dosages formed from this mixture are about 3.5 g. The thermal conversion of gingerol into a gingerol and shogaol combination results in a ratio of gingerol to shogaol by weight in the typical range of 2.0 to 10.0, preferably from 3.0 to 5.0, and most preferably from about 3.6 to 4.6, with 4 being an average value. The increased shogaol concentration creates a more pungent combination that must be taken into account for palatability purposes. The Scoville Heat Units (HSU) of shogaol is 160,000 SHU as opposed to 60,000 SHU for gingerol. This increased pungency limits the concentration of shogaol in the dosage, and thus the amount of 10% gingerol non-volatile extract that can be utilized. For instance, piperine, the pungency compound of black pepper, has 100,000 SHU, making shogaol much more pungent than the spice. This constraint helped shape the ideal embodiment of the present invention.

In a preferred embodiment, the botanical derivative is combined with a natural flavoring, where the concentration of the flavoring is less than or equal to 1.0 wt. %, which provides improved palatability.

EXAMPLES OF THE INVENTION

The biologically active botanical derivative (non-volatile ginger extract with 10% gingerol) may be infused into the simple sugar base in a range of 0.01% to 5.0% by weight. In the current invention, the 10% gingerol non-volatile extract is infused into the molten, desiccated sugar matrix at a typical range of 0.25% to 0.5% by weight, resulting in 0.025% to 0.05% of gingerol active added. Table 1 provides an embodiment of a typical sugar base suitable for the present invention.

TABLE 1

| Base Formula | |
|---|---|
| Ingredients | Percentage |
| Brown rice syrup | 45-55% |
| Dried cane syrup | 45-55% |
| Citric acid | 0-1% |
| Natural flavors | < or = 1% |
| Active ingredients | Listed below |

Method of Preparation of Botanical Derivative Dosages:

The sugar base, ideally in the form of syrup, described in Table 1 is heated on a heat source. This heating continues until the water content of the sugar base is less than about 5% by weight, ideally in the 0.5 to 1.5% by weight range. This degree of desiccation occurs at temperatures in the range of 270° F.-310° F. range, with preferred values in the 300° F.-310° F. range. This temperature is important in order to desiccate the sugar to the desired water percentage, as well as for the thermal conversion of active botanical derivatives. Once removed from the heat source, the active botanical derivative is immediately mixed until a uniform matrix is formed. In example 1, the 10% gingerol non-volatile extract of Zingiber officinale is added during this mixing stage. The high temperatures in the above range, which greatly exceed the normal boiling point of water at 212° F., allow for a unique method of thermal conversion a proportion of the gingerol into shogaols with a stable, high temperature condition. Prior studies have shown that production of shogaols increases in dry, high temperature conditions. Many processing techniques utilize steam, which cannot exceed 212° F. and is incongruous with dry conditions. Supercritical $CO_2$ extraction occurs in low temperatures. The high temperatures and desiccation conditions of the invention provide a novel method for conversion of gingerols to shogaols in a controlled and stable environment. Moreover, the resulting sugar matrix provides additional benefits against spoilage and degradation of desirable bioactive compounds. The high percentage by weight of gingerol in the non-volatile extract, coupled with the high temperatures, and inherent timing of ambient cooling of the invention provide a unique composition of gingerol and shogaol. Moreover, the desiccated sugar matrix and oval shaped dosage minimize degradation of the active compounds that occurs in the presence of moisture and air exposure. In addition, the desiccated nature and extremely high sugar content of the sugar matrix is highly resistant to spoilage. Variations on the invention such as rapid or delayed cooling of the heated mixture can provide for different gingerol to shogaol ratios. The ambient cooling (typical ambient temperature defined as 50° F. to 80° F.), provides the ideal ratio of gingerol to shogaol in the finished dosage, as well as provides adequate time for shaping into the 3.5 g dosage.

Several experiments were performed to optimize the specifications of the present invention. A panel of 5 adults evaluated the following dosages.

In one experiment, different amounts of the 10% gingerol by weight non-volatile *Zingiber officinale* extract were added to the sugar base. For doses of 5.0 mg and 2.5 mg, the dosages were deemed unpalatable secondary to intense pungency (Controls 2 and 3). Below 1.0 mg, the panel concluded that there was diminished clinical efficacy (Control 4). Dosage sizes above 3.5 g created negative organoleptic secondary to large dosage sizes (Control 1). The ideal embodiment of the invention was dosage size of 3.5 g (1.5 mg), and ratio of gingerol to shogaol in the final dosage of 4. (Example 1).

TABLE 2

| Sample | Botanical Derivative | Major Active, Wt. % | Total wt. of Dose (g) | Dose of Active: Gingerol and Shogaol (mg) | Comments |
|---|---|---|---|---|---|
| Control 1 | Zingiber officinale non-volatile extract | 10% gingerol | 5.4 | 4.9 | Dose too large leading to cumulative negative organoleptic |
| Control 2 | Zingiber officinale non-volatile extract | 10% gingerol | 3.5 | 5.0 | Ideal dose size, too pungent to tolerate |
| Control 3 | Zingiber officinale non-volatile extract | 10% gingerol | 3.5 | 2.5 | Too pungent |
| Example 1 | Zingiber officinale non-volatile extract | 10% gingerol | 3.5 | 1.5 | Soothing and acceptable |
| Control 4 | Zingiber officinale non-volatile extract | 10% gingerol | 3.5 | 1.0 | Not soothing |

Analysis of Example 1 for Gingerols and Shogaols

| Gingerols and Shogaols | Detected (mg) |
|---|---|
| 6-Gingerol | 0.618 |
| 8-Gingerol A | 0.171 |
| 6-Shogaol | 0.200 |
| 10-Gingerol | 0.244 |
| 8-Shogaol | 0.0822 |
| Total | 1.3152 |

The Gingerol:Shogaol Ratio for Example 1 is 1.033:0.2822 or 3.66.

Clinical Data

Design

Subjects who experienced at least one digestive complaint in the 3 weeks leading up to enrollment were recruited for a three week open-label study of Example 1.

Subjects were instructed to take the invention when they experienced digestive upsets. If the subjects did not experience symptoms on a daily basis, they were asked to take the inventions on a daily basis regardless. Subjects were asked record their responses in two forms. One was with a visual analog scale (VAS) where they would mark on a scale of zero (worst) to 100 (best) how they felt overall during the week of study. For subjects who experienced digestive upsets during the study period, they were also asked if they had rapid improvement of their digestive complaints after taking the invention in a simple yes/no answer.

The data supported a statistically significant improvement in digestive symptoms in subjects taking the invention, with subjects reporting improvement of symptoms with the invention ($p=0.001$). Subset analysis of individual digestive complaints showed significant improvements in pain, bloating, and urgency ($p<0.001$)

A second retrospective clinical trial was also performed. For the second trial, subjects were recruited for a survey based study. Subjects were asked to report if the dose assisted with intermittent, common digestive complaints. 117 subjects reported benefit from their digestive complaints with use of the invention (90%, $p<0.0001$). The most common reasons for use of the invention were morning sickness (29%), nausea (27%), dyspepsia (18%), and motion sickness (15%). Statistically significant improvements in subjective reports of digestive discomfort were seen in subjects taking ginger dosages for pregnancy related nausea (morning sickness), motion sickness, nausea, and dyspepsia ($p<0.01$-$p<0.001$). There was a trend towards a statistically significant improvement in nausea from post-operative nausea. The study, however, was not adequately powered for these endpoints.

FIG. 1 is a flowchart of a method 100 for forming the invention for treating digestive disorders. The desiccated simple sugar matrix releases active compounds from a botanical derivative rapidly into the body through buccal delivery to thereby provide swift relief of common digestive upsets including cramping, urgency, stomach upset, nausea, and bloating. At step 102, a sugar base is provided. The sugar base may be provided in a syrup form. Optionally, the sugar base may be provided in a solid or crystallized form that is melted. In one embodiment, the sugar base includes at least one of sugar from a source including at least one cane syrup, brown rice syrup, or corn syrup, or a sugar-free base including isomalt. Optionally, the sugar base may be a sugar alcohol base, such as isomalt.

The sugar base may be heated to an acceptable temperature to drive residual moisture below 5%, ideally 0.5% to 1.5% by weight, and for being infused with active agents, at step 104. For example, the sugar base may be heated to as much as 325 degrees F. In an embodiment where the sugar base is provided in a syrup form, the syrup may be heated directly. Alternatively, the syrup may not be required to be heated to infuse the active agent. In an embodiment where the sugar base is provided in a solid or crystallized form, the sugar base may first be melted, at step 106, to form syrup or a heated liquid. The syrup or heated liquid may then be heated for infusion, at step 104.

At step 108, the sugar base is infused with a botanical derivative containing an active agent. The active agent is a non-volatile extract of Zingiber officinale containing at least 10% gingerol by weight. The active agent is infused into the sugar base in a concentration that allows for an acceptable organoleptic profile and efficacy for relief of above stated digestive symptoms. The concentration of the botanical derivative ranges from about 0.1 to 5.0% by weight. The amount of active per dose is from about 1.0 to 5.0 mg.

The sugar base is infused with the active agent after the heat is removed from the carbohydrate base, but while the temperature is still high enough for mixing the carbohydrate base and the active agent. Optionally at least one additional flavoring can be added.

Natural flavoring may be infused with the botanical derivative. The sugar base and the active agent are mixed to form a substantially uniform confection mixture. During this mixing step at elevated temperatures, there is thermal conversion of gingerol into a combination of gingerol and shogaol. In one embodiment, the ratio by weight of gingerol to shogaol in the dosage ranges from 4.6 to 5.6. In one embodiment, the ratio by weight of gingerol to shogaol in the dosage has an average of 4.0. At step 110, the sugar mixture is cooled at ambient temperatures to form the hard sugar matrix. When ingested, the invention is configured to dissolve into saliva through normal human physiologic prehension process. Although some active botanical derivatives are swallowed, the rich vascular supply of the buccal cavity provide for the rapid absorption of active compounds into systemic circulation. The hard dosage maintains its organoleptic perspective when ingested.

The desiccated sugar invention containing 10% gingerol by weight non-volatile extract from Zingiber officinale contains active compounds in a specific ratio, including gingerol and shogaol. These derivatives may assist with nausea, dyspepsia, and motion sickness when ingested. The ginger extract may have at least a partial effect as an antagonist on 5HT-3 receptors in the brain that are implicated in nausea. When a person allows the invention to dissolve in their mouth, the active ingredients enter the bloodstream, and exert at least part of their mechanism on 5HT-3 receptors to provide relief for stomach upset and nausea.

At step 112, the invention is administered. According to a method of administering the dosage, when a person experiences digestive upsets, they may place the invention containing the botanical derivative into their mouth. The normal human digestive processes of the mouth, including mixing of the invention with saliva, may dissolve the confection and, with it, the active compounds. The blood flow through the buccal membranes may then provide for the rapid absorption of the active ingredients to enter the body and act at specific receptors that are implicit to the digestive complaints.

Exemplary embodiments of a desiccated sugar base dosage, a method of forming a desiccated sugar base dosage, and a method of administering a desiccated sugar base dosage are described above in detail. The ingredients and method steps illustrated are not limited to the specific embodiments described herein, but rather, the ingredients and method steps may be utilized independently and separately from other components described herein.

For example, the exact composition of the sugar base may be modified. Moreover, the method could be modified by adjusting the ingredients to provide for more rapid dissolution of the sugar base, thereby enabling more rapid release of the active compounds into the body.

Furthermore, different botanical derivatives with distinct anticipated health benefits could be used in the sugar base in addition to 10% gingerol by weight non-volatile Zingiber officinale. Different products that utilize the same delivery system, but employing distinct botanical derivatives, may also be produced. Other botanicals include, but are not limited to cinnamon, fennel, turmeric, caraway, rosemary, lavender, cardamom, coriander, star anise, and lemongrass.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for preparing a solid buccal dosage form for assisting with the relief of common digestive complaints, the method comprising:
   heating a sugar base to a temperature range of from 270 to 310° F. to create a heated and desiccated sugar base;
   removing the heated base from the heat source;
   immediately adding a non-volatile ginger extract containing gingerol into the heated and dessicated sugar base to form a sugar mixture;
   mixing the heated and dessicated sugar base and the ginger extract to form a uniform heated mixture; and
   cooling the heated mixture at ambient temperature to form a delivery system,
   wherein the gingerol and shogaols are present in the solid dosage form in a concentration of from about 0.025 wt. % to about 0.050 wt. %,
   wherein the delivery system is not encapsulated,
   wherein the heated and dessicated sugar base has a water content of less than or equal to about 5 wt. %, and
   wherein the non-volatile ginger extract contains at least about 10 wt. % gingerol when added to the heated and dessicated sugar base.

2. The method of claim 1, wherein the gingerol in the non-volatile ginger extract is converted to a mixture of gingerol and shogaols in the heated and dessicated sugar.

3. The method of claim 2, wherein the ratio of gingerol to shogaols is in the range of from 2:1 to 10:1.

4. The method of claim 3, wherein combined desiccated sugar base, gingerol and shogaols in the solid dosage form is in the range of about 1.0 to 5.4 g.

5. The method of claim 4, wherein the solid dosage form contains about 0.25 to about 2.7 mg gingerol and shogoals.

* * * * *